United States Patent
Yamada et al.

(10) Patent No.: US 9,352,173 B2
(45) Date of Patent: May 31, 2016

(54) TREATMENT DEVICE

(71) Applicant: Olympus Corporation, Tokyo (JP)

(72) Inventors: Masashi Yamada, Sagamihara (JP); Norihiro Yamada, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

(21) Appl. No.: 14/513,874

(22) Filed: Oct. 14, 2014

(65) Prior Publication Data

US 2015/0119761 A1    Apr. 30, 2015

Related U.S. Application Data

(63) Continuation of application No. PCT/JP2013/083167, filed on Dec. 11, 2013.

(60) Provisional application No. 61/736,811, filed on Dec. 13, 2012.

(51) Int. Cl.
*A61B 17/32* (2006.01)
*A61N 7/00* (2006.01)
*A61B 18/14* (2006.01)
*A61B 18/00* (2006.01)

(52) U.S. Cl.
CPC .......... *A61N 7/00* (2013.01); *A61B 17/320092* (2013.01); *A61B 18/1445* (2013.01); *A61B 2018/0063* (2013.01); *A61N 2007/0004* (2013.01)

(58) Field of Classification Search
CPC ............... A61N 7/00; A61B 17/22004; A61B 17/2202; A61B 17/32; A61B 17/320092; A61B 17/320068; A61B 2017/2207; A61B 2017/320072; A61B 2017/320076; A61B 2017/320088; A61B 2018/00595; A61B 2018/00601; A61B 2018/00607; A61B 2018/0063
See application file for complete search history.

(56) References Cited

U.S. PATENT DOCUMENTS 6,129,735 A      10/2000   Okada et al.
2006/0247558 A1  11/2006   Yamada
2009/0248051 A1  10/2009   Masuda

FOREIGN PATENT DOCUMENTS

JP     A-3-21232      1/1991
JP     A-11-113922    4/1999

(Continued)

OTHER PUBLICATIONS

International Search Report issued in PCT/JP2013/083167 mailed Mar. 18, 2014 (with translation).

(Continued)

*Primary Examiner* — Jonathan W Miles
*Assistant Examiner* — Kankindi Rwego
(74) *Attorney, Agent, or Firm* — Oliff PLC

(57) ABSTRACT

A treatment device includes a treatment portion, a transmission portion and a moment shift portion. The treatment portion transmits ultrasonic vibration. The length of the treatment portion is shorter than ¼ of a wavelength of the ultrasonic vibration. The transmission portion has one end at a node position where the first generated node from the distal end of the treatment portion appears, and is located closer to a proximal side than the node position. The length of the transmission portion is ¼ of the wavelength. The moment shift portion is located between the treatment portion and the transmission portion. An average of $I_1/A_1^2$ is greater than an average of $I_2/A_2^2$, where $I_1$ is the second moment of area and $A_1$ is a sectional area in the treatment portion, and $I_2$ is the second moment of area and $A_2$ is a sectional area in the transmission portion.

9 Claims, 9 Drawing Sheets

(56) References Cited

FOREIGN PATENT DOCUMENTS

| JP | A-2002-85420 | 3/2002 |
| JP | A-2005-57583 | 3/2005 |
| JP | A-2005-304685 | 11/2005 |
| JP | A-2009-240773 | 10/2009 |

OTHER PUBLICATIONS

Jun. 25, 2015 International Preliminary Report on Patentability issued in International Patent Application No. PCT/JP2013/083167.

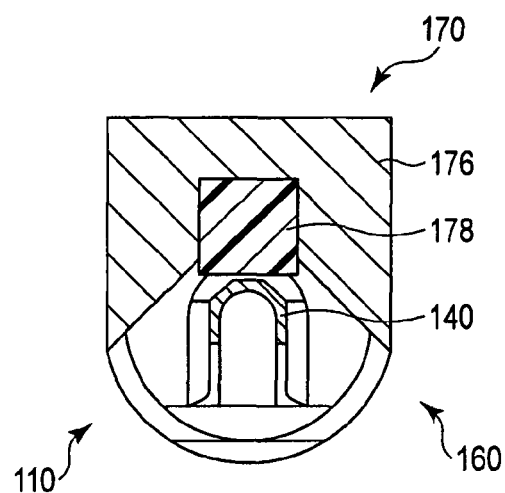
F I G. 4
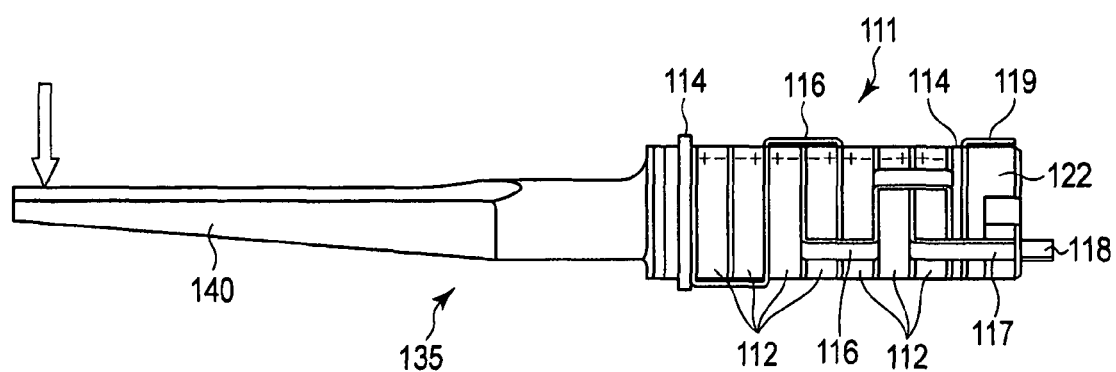
F I G. 5

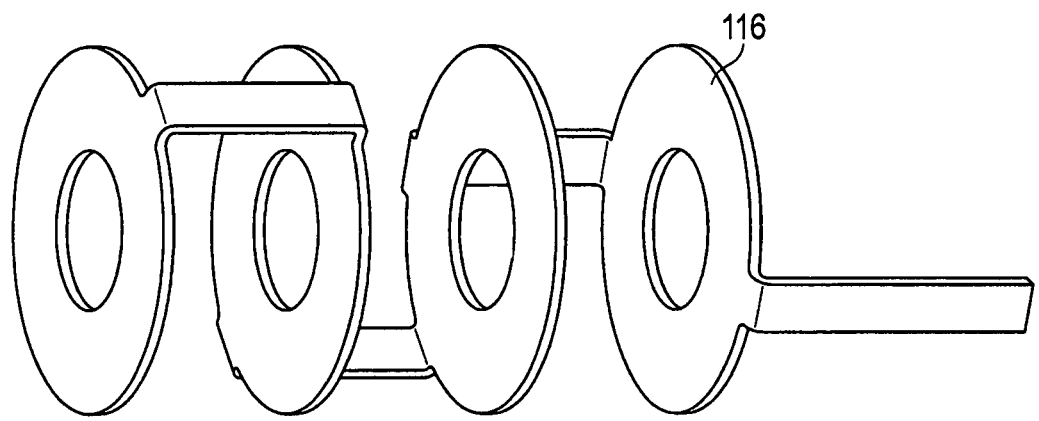
F I G. 6
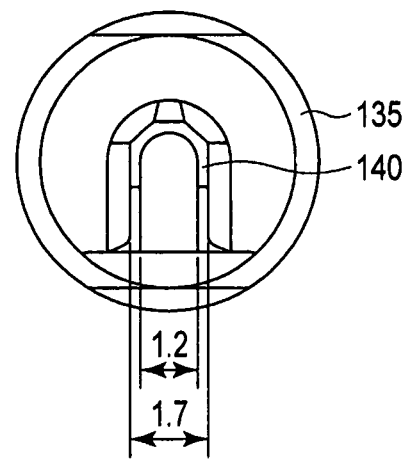
F I G. 7

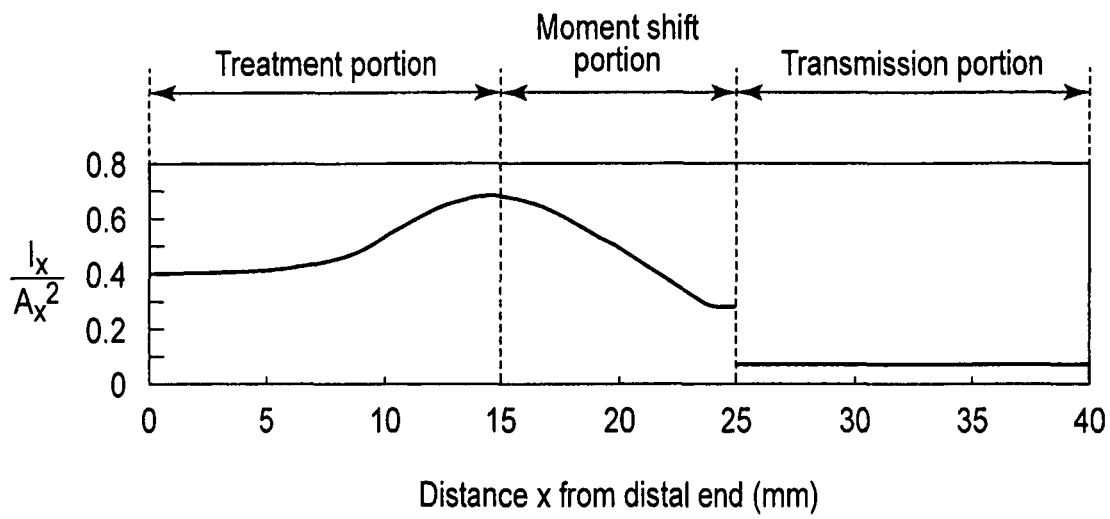
F I G. 10
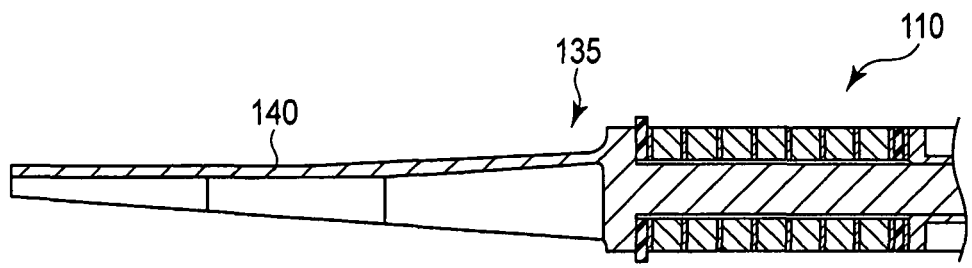
F I G. 11
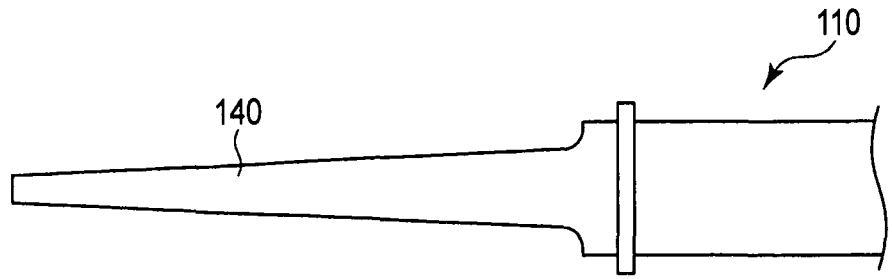
F I G. 12

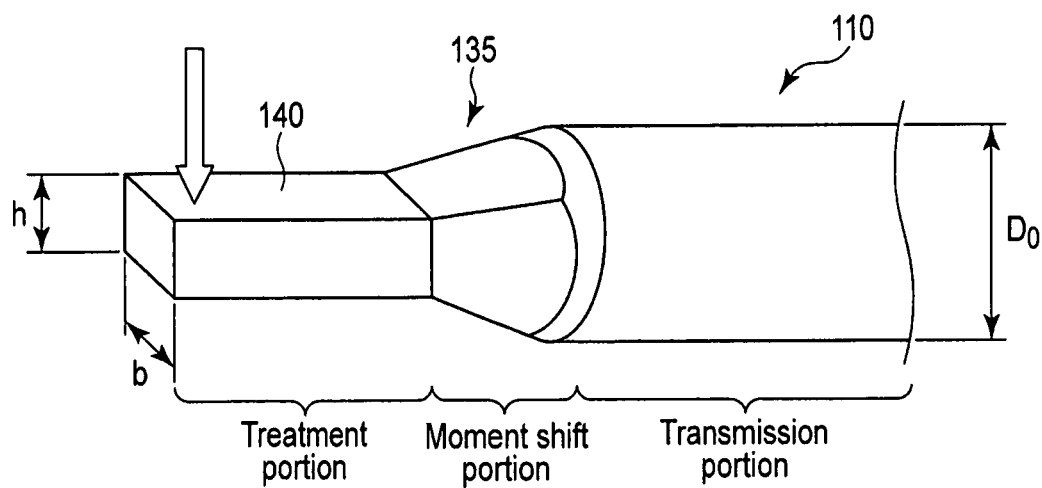
F I G. 13
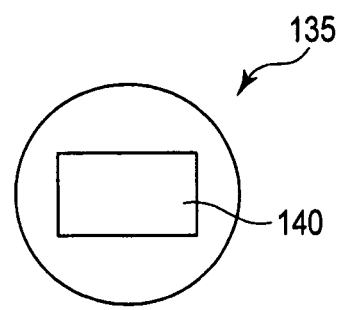
F I G. 14

TREATMENT DEVICE

CROSS-REFERENCE TO RELATED APPLICATIONS

This application is a Continuation application of PCT Application No. PCT/JP2013/083167, filed Dec. 11, 2013 and based upon and claiming the benefit of priority from prior U.S. Provisional Application No. 61/736,811, filed Dec. 13, 2012, the entire contents of all of which are incorporated herein by reference.

BACKGROUND OF THE INVENTION

1. Field of the Invention

The present invention relates to a treatment device.

2. Description of the Related Art

There has been generally known an ultrasonic treatment device which grasps a living tissue with a probe for transmitting ultrasonic vibration and with a grasp member, and which coagulates and cuts the grasped living tissue by the ultrasonic vibration of the probe. An example of such an ultrasonic treatment device is disclosed in, for example, Jpn. Pat. Appln. KOKAI Publication No. 11-113922. Jpn. Pat. Appln. KOKAI Publication No. 11-113922 discloses that the value of the section modulus of the probe is higher in the proximal part than in the distal part to improve the strength of the probe.

BRIEF SUMMARY OF THE INVENTION

According to an aspect of the invention, a treatment device includes: a treatment portion which has a distal end and which transmits ultrasonic vibration generated in an ultrasonic vibrator in a longitudinal direction, a length of the treatment portion from the distal end being shorter than ¼ of a wavelength of the ultrasonic vibration, and the treatment portion being used for grasping a living tissue; a transmission portion having one end at a node position where the node position is a position where a first generated node from the distal end of the treatment portion appears, the transmission portion being located closer to a proximal side than the node position, and a length of the transmission portion being ¼ of the wavelength of the ultrasonic vibration; and a moment shift portion located between the treatment portion and the transmission portion, the moment shift portion causing an average value of $I_1/A_1^2$ of the treatment portion to be greater than an average value of $I_2/A_2^2$ of the transmission portion, where $I_1$ is a second moment of area in the treatment portion calculated with respect to an axis perpendicular to a straight line passing through a barycenter of the treatment portion in a section perpendicular to a longitudinal axis of the transmission portion, $A_1$ is a sectional area in the treatment portion, $I_2$ is a second moment of area in the transmission portion, and $A_2$ is a sectional area in the transmission portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a diagram showing a configuration example of a distal treatment portion according to the first embodiment;

FIG. 5 is a diagram showing a configuration example of an ultrasonic vibrator according to the first embodiment;

FIG. 6 is a diagram showing a configuration example of electrode members according to the first embodiment;

FIG. 7 is a diagram showing a configuration example of an ultrasonic wave transmission member according to the first embodiment;

FIG. 10 shows an example of the relation between the distance from the distal end of the treatment portion and the value of the second moment of area divided by the square of the sectional area according to the first embodiment;

FIG. 11 shows a configuration example of an ultrasonic wave transmission member according to a modification of the first embodiment;

FIG. 12 is a diagram showing a configuration example of a probe according to the modification of the first embodiment;

FIG. 13 is a diagram illustrating a configuration example of an ultrasonic wave transmission member according to a second embodiment;

FIG. 14 is a diagram illustrating a configuration example of the ultrasonic wave transmission member according to the second embodiment;

DETAILED DESCRIPTION OF THE INVENTION

First Embodiment

Figure 1:
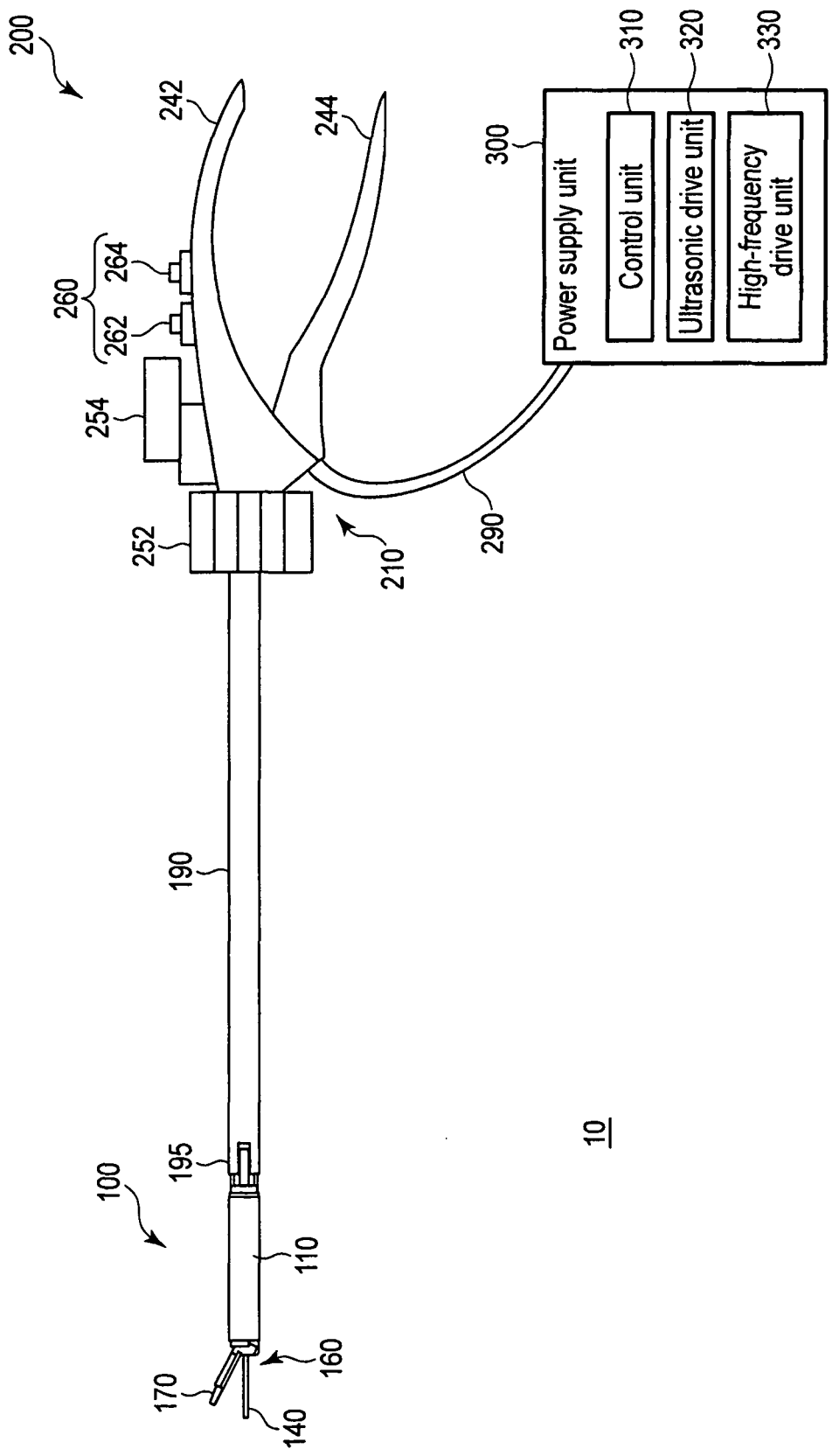
FIG. 1 is a diagram showing a configuration example of a treatment apparatus according to one embodiment.
Figure 2:
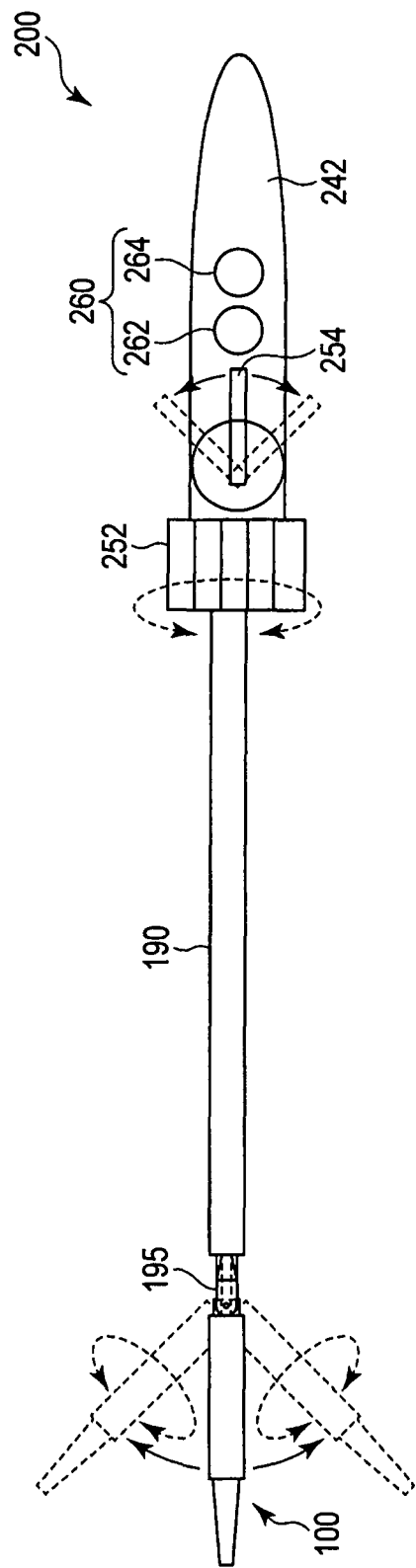
FIG. 2 is a top view showing a configuration example of a treatment portion, a shaft, and an operation portion according to the embodiment.

A first embodiment of the present invention is described with reference to the drawings. A treatment apparatus 10 according to the present embodiment is schematically shown in FIG. 1. As shown in FIG. 1, the treatment apparatus 10 comprises a treatment portion 100, a shaft 190, an operation portion 200, and a power supply unit 300. For the sake of explanation, hereinafter, the side of the treatment portion 100 is referred to as a distal side, and the side of the operation portion 200 is referred to as a proximal side. In FIG. 1, the side view of the treatment portion 100, the shaft 190, and the operation portion 200 is shown. The top view of the treatment portion 100, the shaft 190, and the operation portion 200 is shown in FIG. 2.

The treatment apparatus 10 according to the present embodiment is used in, for example, endoscopic surgery. The treatment portion 100 and the shaft 190 are inserted into, for example, an abdominal cavity through a small hole made in the abdominal wall of a subject. A surgeon operates the operation portion 200 outside the body of the subject to actuate the treatment portion 100. Thus, the shaft 190 is elongated.

The treatment portion 100 of the treatment apparatus 10 grasps a living tissue such as a blood vessel which is a target for treatment. The treatment portion 100 passes a high-frequency current through the grasped living tissue to seal or coagulate the living tissue. The treatment portion 100 also cuts the grasped living tissue while, for example, sealing the living tissue by using ultrasonic vibration.

The treatment portion 100 includes an ultrasonic vibrator 110, a probe 140 and a jaw 170, the probe 140 being a part of an ultrasonic wave transmission member for transmitting ultrasonic waves generated in the ultrasonic vibrator 110. The ultrasonic vibrator 110 has a configuration in which piezoelectric elements are stacked as described later, and generates ultrasonic vibration. The probe 140 is provided on the distal side of the ultrasonic vibrator 110, and is elongated. The probe 140 transmits the ultrasonic vibration generated in the ultrasonic vibrator 110, and vibrates in its longitudinal direction. The jaw 170 moves to open and close relative to the probe 140. The probe 140 and the jaw 170 grasp the living tissue targeted for treatment. Thus, a distal treatment portion 160 is formed by the probe 140 and the jaw 170. Part of the probe 140 and part of the jaw 170 also function as bipolar electrodes for applying a high-frequency voltage to the grasped living tissue.

A joint 195 is provided at the junction of the treatment portion 100 and the shaft 190. The direction of the treatment portion 100 relative to the shaft 190 changes owing to the joint 195. The treatment portion 100 also has a rotary mechanism which is located closer to the distal end than the joint 195 and which rotates around the longitudinal axis relative to the shaft 190.

The operation portion 200 includes an operation portion body 210, a fixed handle 242, a movable handle 244, a rotary knob 252, a joint knob 254, and an output switch 260. The fixed handle 242 is fixed to the operation portion body 210, and the movable handle 244 is displaced relative to the operation portion body 210. The operation of the movable handle 244 is transmitted to the jaw 170 via the shaft 190. The jaw 170 is displaced relative to the probe 140 in response to the operation of the movable handle 244. As a result, the distal treatment portion 160 opens and closes.

The rotary knob 252 is a knob to rotate the treatment portion 100 around the longitudinal axis. As shown in FIG. 2, the rotary mechanism provided in the treatment portion 100 operates in response to the operation of the rotary knob 252, and the treatment portion 100 rotates. The joint knob 254 is a knob to drive the joint 195. The joint 195 operates in response to the displacement of the joint knob 254, and the direction of the treatment portion 100 relative to the shaft 190 changes.

The output switch 260 includes a first switch 262 and a second switch 264. When the first switch 262 is pressed, the first switch 262 outputs a signal which allows the treatment portion 100 to be driven by the ultrasonic vibrator. As a result, the probe 140 of the treatment portion 100 ultrasonically vibrates, and the living tissue grasped by the distal treatment portion 160 is cut. When the second switch 264 is pressed, the second switch 264 outputs a signal which allows the treatment portion 100 to apply a high-frequency voltage and be driven by the ultrasonic vibrator. As a result, the high-frequency voltage is applied to the distal treatment portion 160, and the living tissue grasped by the distal treatment portion 160 is sealed or coagulated. Moreover, the probe 140 ultrasonically vibrates, and the living tissue grasped by the distal treatment portion 160 is cut.

One end of a cable 290 is connected to the operation portion 200. The other end of the cable 290 is connected to the power supply unit 300. The power supply unit 300 includes a control unit 310, an ultrasonic drive unit 320, and a high-frequency drive unit 330. The control unit 310 controls each component of the treatment apparatus 10. For example, the control unit 310 controls the operations of the ultrasonic drive unit 320 and the high-frequency drive unit 330 in response to an input from the output switch 260. The ultrasonic drive unit 320 drives the ultrasonic vibrator 110 under the control of the control unit 310. The high-frequency drive unit 330 supplies a high-frequency current to the distal treatment portion 160 under the control of the control unit 310.

The operation of the treatment apparatus 10 according to the present embodiment is described. The surgeon operates an input unit of the power supply unit 300 to set output conditions of the treatment apparatus, such as output electric power of high-frequency energy and output electric power of ultrasonic energy. The treatment apparatus 10 may be configured so that each value is individually set or may be configured so that a set of set values corresponding to a surgical method are selected.

The treatment portion 100 and the shaft 190 are inserted into, for example, an abdominal cavity through an abdominal wall. The surgeon operates the rotary knob 252 and the joint knob 254 to bring the treatment portion 100 closer to the living tissue targeted for treatment. The surgeon operates the movable handle 244 to open and close the treatment portion 100, and grasps the treatment target living tissue by the probe 140 and the jaw 170. The treatment target living tissue may be, for example, a blood vessel. Various tissues are conceivable as living tissues other than a blood vessel.

After having grasped the treatment target living tissue with the treatment portion 100, the surgeon operates the output switch 260. For example, when the second switch 264 is pressed, the second switch 264 outputs a signal which allows the treatment portion 100 to apply a high-frequency voltage and drive the ultrasonic vibrator. The control unit 310 of the power supply unit 300 which has acquired the signal outputs a driving instruction to the ultrasonic drive unit 320 and the high-frequency drive unit 330.

The high-frequency drive unit 330 applies a high-frequency voltage to the probe 140 and the jaw 170 of the treatment portion 100 under the control of the control unit 310, and passes a high-frequency current through the treatment target living tissue. As living tissue has electrical resistance, when the high-frequency current is passed through it, heat is generated in the living tissue, and the temperature of the living tissue increases. The temperature of the living tissue at this moment reaches, for example, 100° C. to 200° C. As a result, protein is denatured, and the living tissue is coagulated and sealed.

The ultrasonic drive unit 320 drives the ultrasonic vibrator 110 under the control of the control unit 310. As a result, the probe 140 vibrates in its longitudinal direction at an ultrasonic frequency. The temperature of the living tissue increases due to frictional heat of the living tissue and the probe 140. As a result, protein is denatured, and the living tissue is coagulated and sealed. The effect of sealing the living tissue by the ultrasonic vibration is lower than the sealing effect by the application of the high-frequency voltage. The temperature of the living tissue reaches, for example, 200° C. As a result, the living tissue is dissolved, and the living tissue is cut. In this way, the living tissue grasped by the distal treatment portion 160 is cut while being coagulated and sealed. Consequently, the treatment for the living tissue is completed.

Figure 3:
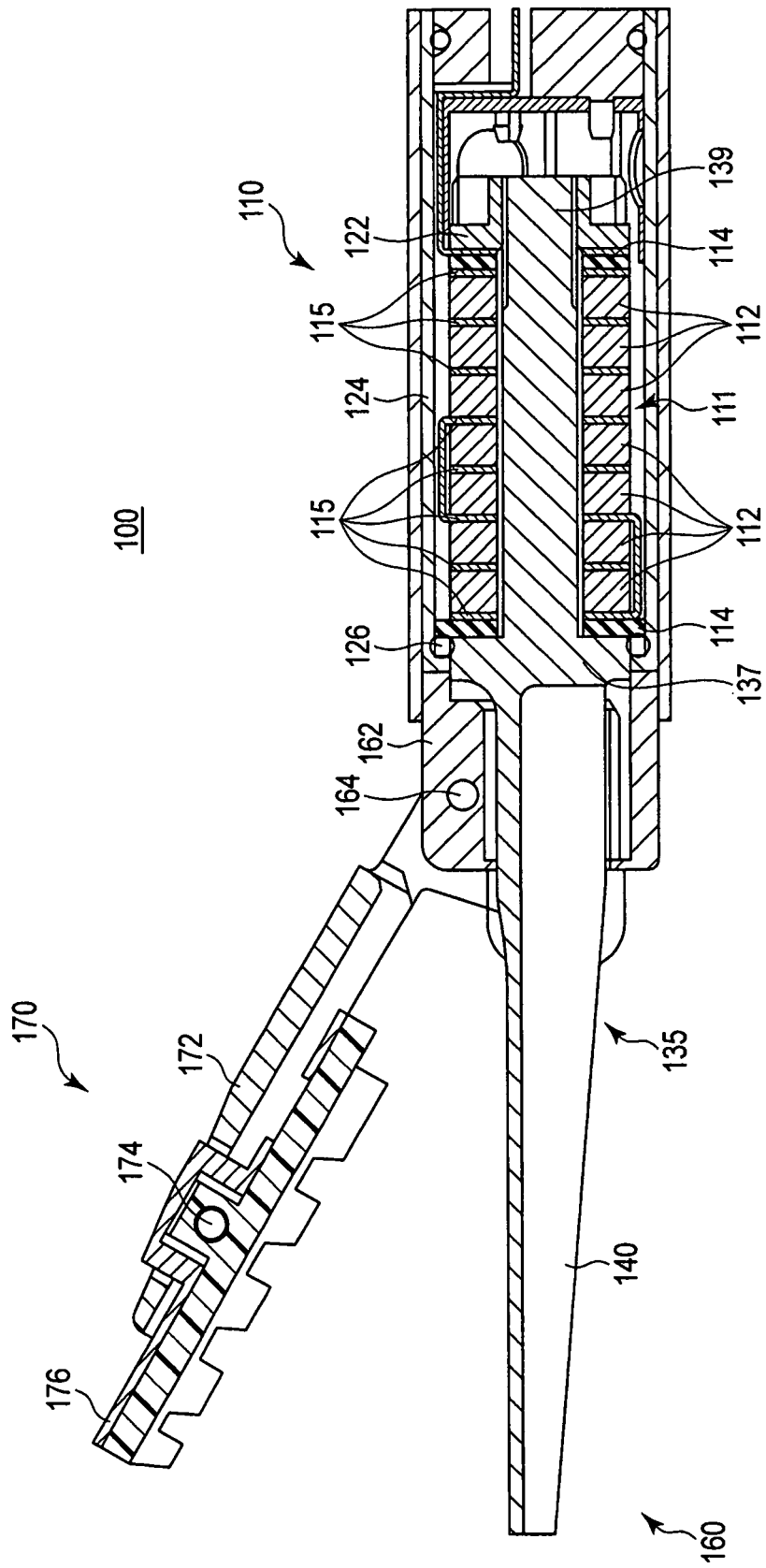
FIG. 3 is a diagram showing a configuration example of the treatment portion according to a first embodiment.

The treatment portion 100 is further described with reference to FIG. 3. As shown in FIG. 3, the ultrasonic vibrator 110 includes seven piezoelectric elements 112. These piezoelectric elements 112 are ring-shaped, and are stacked across ring-shaped electrodes 115, respectively. Ring-shaped insulating boards 114 are provided at both ends of the ultrasonic vibrator 110. Thus, the ring-shaped piezoelectric elements 112, the electrodes 115, and the insulating boards 114 are stacked, so that a vibrating member 111 having a hollow cylindrical shape as a whole is formed.

The treatment portion 100 includes an ultrasonic wave transmission member 135. The distal side of the ultrasonic wave transmission member 135 forms the probe 140. A projection 137 is provided at the proximal end of the probe 140 of the ultrasonic wave transmission member 135. The vibrating member 111 including the piezoelectric elements 112 and others is pressed against the projection 137. A through portion 139 is provided closer to the proximal end than the projection 137 of the ultrasonic wave transmission member 135. The through portion 139 passes through the center of the cylindrical vibrating member 111. That is, the through portion 139 passes through the piezoelectric elements 112, the insulating boards 114, the electrodes 115, and others. The through portion 139 contacts the piezoelectric elements 112 and the insulating boards 114, but does not contact the electrodes 115. A liner board 122 is provided on the proximal side of the through portion 139. The liner board 122 presses the ultrasonic vibrator 110 against the projection 137 of the ultrasonic wave transmission member 135.

The ultrasonic vibrator 110 is disposed in a cylinder 124. The cylinder 124 serves as a cover for the ultrasonic vibrator 110. An O-ring 126 is provided at the distal end of the cylinder 124. The O-ring 126 seals the clearance between the ultrasonic wave transmission member 135 and the cylinder 124, and thereby prevents any liquid from coming into the cylinder 124. A coupling member 162 is provided on the distal side of the cylinder 124. The coupling member 162 is provided with a support member 172 of the jaw 170 rotatably around a first rotation pivot 164 provided in the coupling member 162.

A second rotation pivot 174 is provided in the vicinity of the distal end of the support member 172, and a grasp member 176 is provided rotatably around the second rotation pivot 174. The grasp member 176 is rotatable relative to the support member 172 in accordance with the position of the support member 172. As a result, the distal treatment portion 160 can grasp the living tissue with the same pressure on the distal side and the proximal side even if the thickness of the living tissue to be grasped varies between the distal side and the proximal side. The application of uniform pressure to the treatment target living tissue is advantageous to the stable sealing, coagulation, and cutting of the living tissue.

The sectional view of the probe 140 and the grasp member 176 seen from the distal side when the distal treatment portion 160 is closed is shown in FIG. 4. As shown in FIG. 4, when the surface of the probe 140 facing the grasp member 176 is a grasp surface, a slot is provided in the surface which is the opposite surface of the grasp surface relative to the central axis of the probe 140, and the section of the probe 140 is U-shaped. That is, the bottom of the U-shape of the probe 140 faces the grasp member 176.

A contact member 178 is provided in the grasp member 176. The contact member 178 is made of an insulating material such as a fluororesin. When the distal treatment portion 160 is closed, the probe 140 contacts with the contact member 178, and a clearance is formed between the probe 140 and the grasp member 176. During the use of the treatment apparatus 10, when the distal treatment portion 160 grasps the living tissue and applies a high-frequency voltage, an electric current runs through the living tissue located in the clearance where the probe 140 and the grasp member 176 face each other. That is, the probe 140 and the grasp member 176 function as bipolar electrodes. As a result, the part of the living tissue through which the electric current has run is sealed and coagulated. When the ultrasonic vibrator 110 vibrates, the probe 140 vibrates in its longitudinal direction, and the part of the living tissue between the probe 140 and the grasp member 176 rubs against the probe 140 and is cut.

The vibrating member 111 of the ultrasonic vibrator 110 is further described with reference to FIG. 5 and FIG. 6. FIG. 6 is a perspective view of electrode members 116 constituting the electrodes 115 provided at both ends of each of the piezoelectric elements 112 of the ultrasonic vibrator 110. As shown in FIG. 5, two electrode members 116 are alternately provided in the ultrasonic vibrator 110. The end of one electrode member 116 is a positive electrode 117, and the end of the other electrode member 116 is a negative electrode 118. For example, when a voltage is applied across the positive electrode 117 and the negative electrode 118, a voltage shown in FIG. 5 is applied across both ends of each of the piezoelectric elements 112. An alternating voltage having a frequency equivalent to ultrasonic waves is thus applied across both ends of each of the piezoelectric elements 112. Accordingly, each of the piezoelectric elements 112 vibrates and generates ultrasonic waves. The ultrasonic vibrator 110 has a stack of seven piezoelectric elements 112, and thus generates a great displacement. Because of the odd number of piezoelectric elements 112, the electrode member used as the positive electrode and the electrode member used as the negative electrode have the same shape as the electrode members 116 shown in FIG. 6. As a result, manufacturing costs can be reduced.

A high-frequency electrode 119 in contact with the ultrasonic wave transmission member 135 is provided between the insulating boards 114 and the liner board 122. A high-frequency voltage is applied to the ultrasonic wave transmission member 135 via the high-frequency electrode 119. As shown in FIG. 5, the insulating boards 114 insulate the ultrasonic wave transmission member 135 from the electrode members 116.

Figure 8:
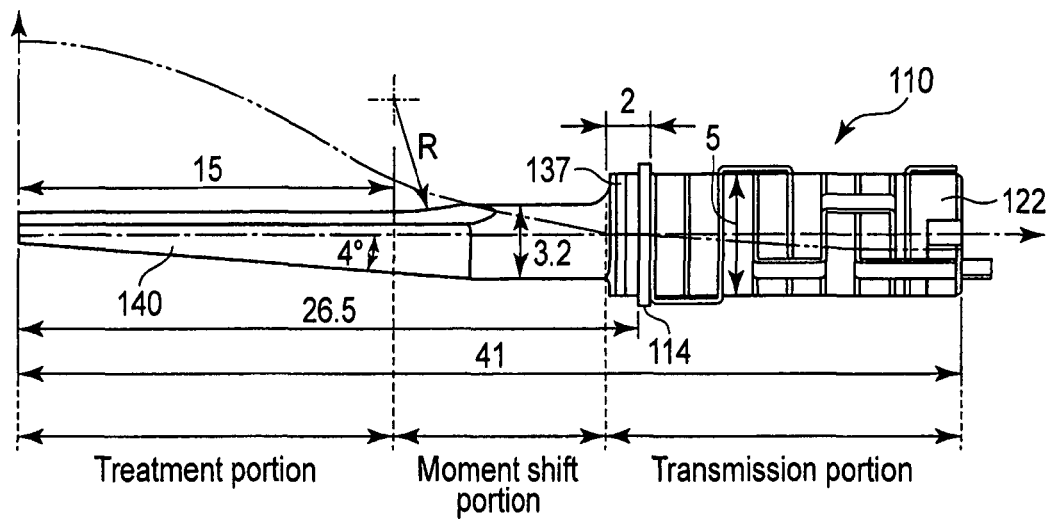
FIG. 8 is a diagram showing a configuration example of the ultrasonic wave transmission member according to the first embodiment.
Figure 9:
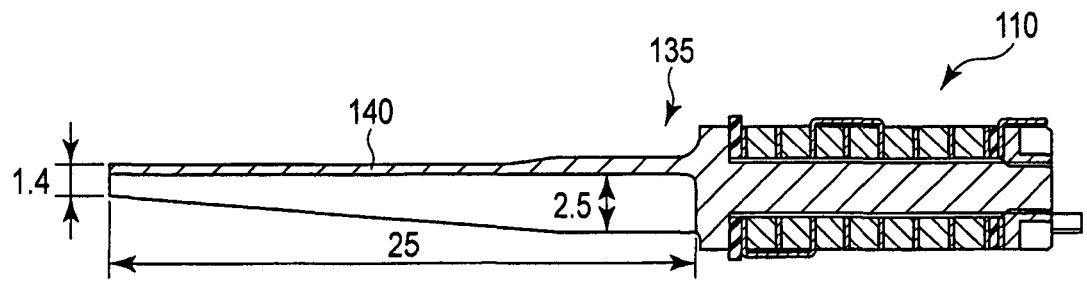
FIG. 9 is a diagram showing a configuration example of the ultrasonic wave transmission member according to the first embodiment.

The dimensions of each part of the ultrasonic wave transmission member 135 and others are shown in FIG. 7 to FIG. 9. The unit of length shown in FIG. 7 to FIG. 9 is millimeters. FIG. 7 is a front view of the ultrasonic wave transmission member 135 seen from the distal side. As shown in FIG. 7, the width of the probe 140 is, for example, 1.7 mm, and the width of the slot provided in the probe 140 is, for example, 1.2 mm.

FIG. 8 is a side view of the ultrasonic wave transmission member 135 and others, and FIG. 9 is a sectional view of the ultrasonic wave transmission member 135 and others. With the origin located at the distal end of the probe 140, the length is defined toward the proximal side. The length of the grasp portion of the probe 140 facing the grasp member 176 is 15 mm. The length from the distal end to the insulating boards 114 is, for example, 26.5 mm. The length of the ultrasonic wave transmission member 135 is, for example, 41 mm. The height of the probe 140 becomes smaller toward the distal end. The grasp surface of the probe 140 facing the grasp member 176 is parallel to the central axis of the longitudinal direction of the ultrasonic wave transmission member 135. On the other hand, the rear surface of the probe 140 opposite to the surface facing the grasp member 176 is tilted, for example, 4° relative to the central axis. The height of the probe 140 at the distal end is, for example, 1.4 mm, and the height of the probe 140 at the proximal end is, for example, 3.2 mm. The depth of the slot in the probe 140 is, for example, 2.5 mm. The bottom of the slot is parallel to the central axis. The outside diameter of the piezoelectric element 112 is, for example, 5 mm. The outside diameter of the shaft 190 is, for example, 10.5 mm.

A two-dot chain line in FIG. 8 indicates the vibration velocity of ultrasonic vibration generated by the ultrasonic vibrator 110. In the present embodiment, a node of vibration is generated in the projection 137 where the ultrasonic wave transmission member 135 contacts the ultrasonic vibrator 110. As shown in FIG. 8, the probe 140 is thinner toward the distal end, so that the vibration velocity increases toward the distal end. In the present embodiment, the vibration frequency is 75 kHz. The vibration velocity at the distal end of the probe 140 is, for example, 18 m/sp-p, and the vibration velocity at the proximal end of the probe 140 is, for example, 1.5 m/sp-p.

In the present embodiment, the grasp portion extending 15 mm from the distal end where the probe 140 faces the grasp member 176 is referred to as a treatment portion. The part which is closer to the proximal end than the treatment portion and which extends to the projection 137, that is, the part extending between 15 mm and 25 mm from the distal end is referred to as a moment shift portion. The part closer to the proximal end than the moment shift portion, that is, the part closer to the proximal end than the projection 137 is referred to as a transmission portion. Thus, the length of the treatment portion is shorter than ¼ of the wavelength of the ultrasonic waves. The length of the transmission portion is ¼ of the wavelength of the ultrasonic waves. The length of the ultrasonic wave transmission member 135 including the part where the ultrasonic vibrator 110 is provided is ½ of the wavelength of the ultrasonic waves.

In the present embodiment, the section of the probe 140 is U-shaped for the following reasons. The probe 140 and the jaw 170 catch the living tissue, so that a grasp load is applied to the probe 140 in the direction of the open arrow shown in FIG. 5. Thus, a probe treatment portion 120 is required to be difficult to bend when the grasp load is applied thereto. On the other hand, the distal end of the probe 140 is required to be thin so that treatment for small parts is possible and so that the vibration velocity of the ultrasonic waves increases at the distal end. In the present embodiment, the section of the probe 140 is U-shaped so that the probe 140 is difficult to bend when the grasp load is applied to the thin probe 140.

Regarding a section perpendicular to the central axis at each position whose distance from the distal end is x, the second moment of area calculated with respect to an axis perpendicular to the grasp load is Ix. A sectional area at each position whose distance from the distal end is x is Ax. That is, when a y-axis is provided parallel to the grasp load direction and a z-axis is provided in a direction perpendicular to the y-axis in the section perpendicular to the central axis, the second moment of area Ix is provided by $$I_x = I_z(x) = \int_{A_x} y^2 dA_x.$$

The relation between the distance x from the distal end of the probe 140 and a value obtained by dividing the second moment of area Ix of the part comprising the probe 140 and the ultrasonic vibrator 110 by the square of the sectional area Ax is shown in FIG. 10. Here, the value obtained by dividing the second moment of area I by the square of the sectional area A is a value obtained when the second moment of area is transformed into a dimensionless state, and represents rigidity per unit sectional area relative to the grasp load. As shown in FIG. 10, the value obtained by dividing the second moment of area Ix at any position of the treatment portion having a U-shaped section by the square of the sectional area Ax is greater than the value obtained by dividing the second moment of area Ix at any position of the transmission portion having a circular section by the square of the sectional area Ax. Therefore, the average of the values obtained by dividing the second moment of area Ix in the treatment portion by the square of the sectional area Ax is greater than the average of the values obtained by dividing the second moment of area Ix in the transmission portion by the square of the sectional area Ax.

In this way, for example, the probe 140 and the ultrasonic vibrator 110 function as an elongated ultrasonic vibrator which ultrasonically vibrates. For example, the jaw 170 functions as a grasp member which moves relative to the ultrasonic vibrator to grasp the treatment target living tissue between the grasp member and the ultrasonic vibrator.

When the section of the probe 140 is U-shaped as in the present embodiment, the value obtained by dividing the second moment of area Ix of the probe 140 in the grasp load direction by the square of the sectional area Ax, that is, the rigidity per unit sectional area is higher than when the sectional shape is circular. Thus, when the section of the probe 140 is U-shaped, the probe 140 that is difficult to bend can be provided. As described above, when the shape of the probe 140 that is desirably thin is properly set as in the present embodiment, the strength of the probe 140 against the grasp load improves.

In the present embodiment, the value obtained by dividing the second moment of area Ix at any position of the treatment portion by the square of the sectional area Ax is greater than the value obtained by dividing the second moment of area Ix at any position of the transmission portion by the square of the sectional area Ax. However, this is not a limitation. If the representative value of the value obtained by dividing the second moment of area Ix in the treatment portion by the square of the sectional area Ax (referred to as $I_1/A_1^2$) is greater than the representative value of the value obtained by dividing the second moment of area Ix in the transmission portion by the square of the sectional area Ax (referred to as $I_2/A_2^2$), advantageous effects similar to the advantageous effects in the present embodiment can be provided. Here, the representative value of the transmission portion can be the average value of the value $I_2/A_2^2$, and the representative value of the treatment portion can be, for example, the value $I_1/A_1^2$ of the part to which higher stress is applied than other parts, the value $I_1/A_1^2$ of the part to which the grasp load is applied, or the value $I_1/A_1^2$ of the part with which the living tissue comes into contact. This is because high rigidity is required in the part to which high stress is applied, the part to which the grasp load is applied, and the part with which the living tissue comes into contact. Therefore, it is not a problem in some cases if the value $I_2/A_2^2$ is lower than the value $I_2/A_2^2$ of the transmission portion, for example, in part of the treatment portion.

Modification of First Embodiment

A modification of the first embodiment of the present invention is described. Here, differences between the modification and the first embodiment are described, and the same parts are provided with the same reference signs and are not described. The sectional view of the ultrasonic vibrator 110 and the ultrasonic wave transmission member 135 according to the present modification is shown in FIG. 11, and the top view thereof is shown in FIG. 12. As shown in FIG. 11 and FIG. 12, the probe 140 according to the present modification is thicker on the proximal side than the probe 140 according to the first embodiment. In the probe 140 according to the present modification, the bottom of the slot is tilted relative to the central axis so that the depth of the U-shaped slot is greater on the proximal side.

The proximal side of the probe 140 having the structure according to the present modification is thicker, so that the stress resulting from the grasp load is dispersed, and the maximum stress associated with the probe 140 is reduced. As a result, the probe 140 according to the present modification is stronger against the grasp load. The U-shaped bottom of the slot is tilted relative to the central axis, and the slot is deeper on the proximal side, so that the sectional area gradually decreases toward the distal end of the probe 140, and the vibration velocity in the treatment portion of the probe 140 is increased.

Second Embodiment

A second embodiment of the present invention is described. Here, differences between the second embodiment and the first embodiment are described, and the same parts are provided with the same reference signs and are not described. The shapes of the ultrasonic wave transmission member 135 and others according to the present embodiment are shown in FIG. 13 and FIG. 14. FIG. 13 is a perspective view showing the shapes of the ultrasonic wave transmission member 135 and others. FIG. 14 is a front view of the ultrasonic wave transmission member 135 and others seen from the distal side. As shown in FIG. 13 and FIG. 14, the probe 140 according to the present embodiment has a quadratic prism shape. Here, the length of the probe 140 in a load direction indicated by an open arrow in FIG. 13 is a height h, and the length in a direction perpendicular to the load direction and the central axis is a width b. Here, the second moment of area $I_1$ associated with the load direction of the probe 140 which is the treatment portion is represented by $I_1=(b \cdot h^3)/12$. A sectional area $A_1$ of the plane perpendicular to the central axis of the probe 140 which is the treatment portion is represented by $A_1=b \cdot h$. Therefore, $I_1/A_1^2=h/12b$.

On the other hand, the sectional shape of the surface perpendicular to the central axis of the transmission portion including the ultrasonic vibrator 110 is a circle having a diameter $D_0$. Here, the second moment of area $I_0$ of the transmission portion is represented by $I_0=\pi D_0^4/64$. A sectional area $A_0$ of the transmission portion is represented by $A_0=\pi D_0^2/4$. Therefore, $I^1/A_0^2=1/4\pi$ is given.

Consequently, when $h/b>3/\pi$, $I_1/A_1^2>I_0/A_0^2$ is achieved. That is, when $h/b>3/\pi$, the rigidity per unit sectional area is higher in the treatment portion than in the transmission portion. That is, when the sectional shape of the probe 140 is $h/b>3/\pi$, the probe 140 is more difficult to bend, and the strength of the probe 140 against the grasp load improves.

Third Embodiment

Figure 15:
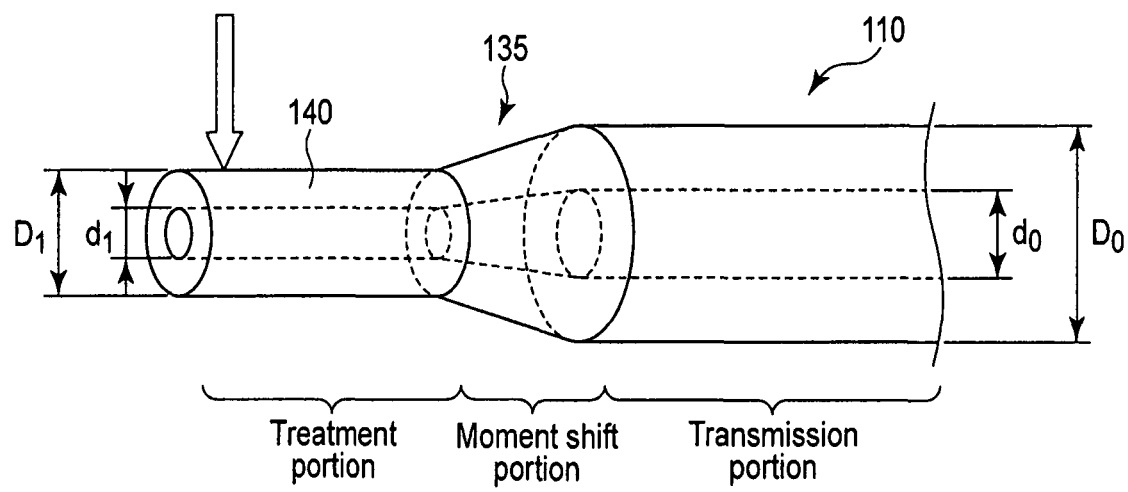
FIG. 15 is a diagram illustrating a configuration example of an ultrasonic wave transmission member according to a third embodiment.
Figure 16:
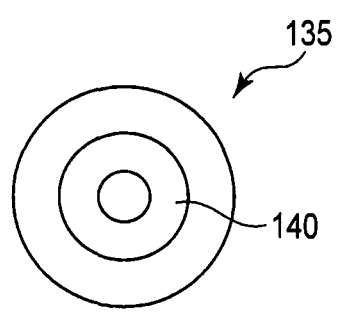
FIG. 16 is a diagram illustrating a configuration example of the ultrasonic wave transmission member according to the third embodiment.

A third embodiment of the present invention is described. Here, differences between the third embodiment and the first embodiment are described, and the same parts are provided with the same reference signs and are not described. The shapes of the ultrasonic wave transmission member 135 and others according to the present embodiment are shown in FIG. 15 and FIG. 16. FIG. 15 is a perspective view showing the shapes of the ultrasonic wave transmission member 135 and others. FIG. 16 is a front view of the ultrasonic wave transmission member 135 and others seen from the distal side. As shown in FIG. 15 and FIG. 16, the probe 140 which is the treatment portion according to the present embodiment has a hollow cylindrical shape. In the present embodiment, the transmission portion also has a cylindrical shape.

The outside diameter of the cylindrical shape of the treatment portion is $D_1$, and the inside diameter thereof is $d_1$. The outside diameter of the transmission portion is $D_0$, and the inside diameter thereof is $d_0$. Here, the second moment of area $I_1$ associated with the load direction of the probe 140 which is the treatment portion is represented by $I_1=(D_1^4-d_1^4)\pi/64$. A sectional area $A_1$ of the plane perpendicular to the central axis of the probe 140 which is the treatment portion is represented by $A_1=(D_1^2-d_1^2)\pi/4$. Therefore, $I_1/A_1^2=(D_1^2+d_1^2)/(8\pi(D_1^2-d_1^2))$ is given.

On the other hand, the second moment of area $I_0$ of the transmission portion including the ultrasonic vibrator 110 is represented by $I_0=(D_0^4-d_0^4)\pi/64$. A sectional area $A_0$ of the transmission portion is represented by $A_0=(D_0^2-d_0^2)\pi/4$. Therefore, $I_0/A_0^2=(D_0^2+d_0^2)/(8\pi(D_0^2-d_0^2))$ is given.

Consequently, when $$(D_1^2+d_1^2)(D_0^2-d_0^2)>(D_1^2-d_1^2)(D_0^2+d_0^2),$$

then $I_1/A_1^2>I_0/A_0^2$ is achieved. That is, when $$(D_1^2+d_1^2)(D_0^2-d_0^2)>(D_1^2-d_1^2)(D_0^2+d_0^2),$$

the rigidity per unit sectional area is higher in the treatment portion than in the transmission portion. That is, when the sectional shape of the probe 140 is $$(D_1^2+d_1^2)(D_0^2-d_0^2)>(D_1^2-d_1^2)(D_0^2+d_0^2),$$

the probe 140 is more difficult to bend, and the strength of the probe 140 against the grasp load improves.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device comprising:
   a treatment portion which has a first distal end portion and a first proximal end portion and which transmits ultrasonic vibration generated in an ultrasonic vibrator from the first proximal end portion to the first distal end portion in a longitudinal direction, a length of the treatment portion from the first distal end portion in the longitudinal direction being portion being used for grasping a living tissue;
   a transmission portion having a second distal end portion, the second distal end portion being located at a node position where the node position is a position where a first generated node from the first distal end portion of the treatment portion appears, a second length of the transmission portion in the longitudinal direction being ¼ of a wavelength of the ultrasonic vibration, and, the transmission portion comprising a piezoelectric element as the ultrasonic vibrator; and
   a moment shift portion located between the treatment portion and the transmission portion, a length of the moment shift portion in the longitudinal direction being a third length, the moment shift portion causing an average value of I1/A12 of the treatment portion to be greater than an average value the I2/A22 transmission portion, where I1 is a second moment of area in the treatment portion calculated with respect to an axis perpendicular to a direction to which a load is applied by grasping the living tissue in a section perpendicular to the longitudinal direction, A1 is a sectional area in the treatment portion, I2 is a second moment of area in the transmission portion, and A2 is a sectional area in the transmission portion, wherein a total length of the first length in the treatment portion and the third length in the moment shift portion is ¼ of the wavelength of the ultrasonic vibration, and the treatment portion and the moment shift portion each have a U-shaped section perpendicular to the longitudinal direction.

2. The treatment device according to claim 1, wherein the value of $I_1/A_1^2$ at any position of the treatment portion is greater than the value of $I_2/A_2^2$ at any position of the transmission portion.

3. The treatment device according to claim 1, wherein the treatment portion functions as a high-frequency electrode, and treats the living tissue by using ultrasonic vibration energy and high-frequency current energy.

4. The treatment device according to claim 1, further comprising:
a grasp member which grasps the living tissue which is a grasp target with the treatment portion, wherein
the treatment portion is shaped to have a slot in a rear surface so that the treatment portion has the U-shaped section when a surface of the treatment portion facing the grasp member is a grasp surface and a surface opposite to the grasp surface relative to the central axis of the treatment portion is the rear surface.

5. The treatment device according to claim 4, wherein
a bottom of the slot is parallel to the central axis of the treatment portion, or the bottom of the slot of a proximal side of the treatment portion is more tilted toward the grasp surface than the bottom of the slot of a distal side of the treatment portion, and
the treatment portion is smaller in a height from the grasp surface to the rear surface on the distal side than on the proximal side.

6. The treatment device according to claim 5, further comprising a joint provided on a proximal side of the ultrasonic vibration unit, wherein
a total length of the ultrasonic vibration unit combining the transmission portion and a probe including the moment shift portion and the treatment portion is ½ of the wavelength of the ultrasonic vibration.

7. The treatment device according to claim 1, further comprising:
a grasp member which grasps the living tissue which is a grasp target with the treatment portion, wherein
a shape of a section perpendicular to the longitudinal direction of the treatment portion is a rectangle having a width b which is a length of a horizontal side facing the grasp member and having a height h which is a length of a side perpendicular to the horizontal side,
a shape of a section perpendicular to the longitudinal direction of the transmission portion is circular, and
the width b and the height h are $h/b > 3/\pi$.

8. The treatment device according to claim 1, wherein
the treatment portion has a cylindrical shape with an outside diameter $D_1$ and an inside diameter $d_1$,
the transmission portion has a cylindrical shape with an outside diameter $D_0$ and an inside diameter $d_0$, and $$(D_1^2 + d_1^2)(D_0^2 - d_0^2) > (D_1^2 - d_1^2)(D_0^2 + d_0^2).$$

9. The treatment device according to claim 1, wherein a probe including the moment shift portion and the treatment portion has a shape being thinner toward a distal end side.

* * * * *